(12) United States Patent
Cui et al.

(10) Patent No.: US 7,220,433 B2
(45) Date of Patent: May 22, 2007

(54) COMPOSITIONS FOR PARENTERAL ADMINISTRATION AND SUSTAINED-RELEASE OF THERAPEUTIC AGENTS

(75) Inventors: Han Cui, Bridgewater, NJ (US); Joel Rosenblatt, Watchung, NJ (US); Ram L. Kataria, Hamilton Square, NJ (US); Chuanbin Wu, Sunrise, FL (US)

(73) Assignee: Ethicon, Inc., Somerville, NJ (US)

( * ) Notice: Subject to any disclaimer, the term of this patent is extended or adjusted under 35 U.S.C. 154(b) by 558 days.

(21) Appl. No.: 10/608,507

(22) Filed: Jun. 27, 2003

(65) Prior Publication Data

US 2004/0265383 A1 Dec. 30, 2004

(51) Int. Cl.
*A61K 9/16* (2006.01)
(52) U.S. Cl. .................. 424/495; 424/400; 424/490; 424/493; 424/494; 424/489; 424/498; 424/502
(58) Field of Classification Search .................. None
See application file for complete search history.

(56) References Cited

U.S. PATENT DOCUMENTS 4,891,223 A * 1/1990 Ambegaonkar et al. .... 424/408

5,328,697 A 7/1994 Raman et al.

FOREIGN PATENT DOCUMENTS

| EP | 1 270 024 A1 | 1/2003 |
|---|---|---|
| EP | 1 374 860 A1 | 1/2004 |
| EP | 1 430 914 A1 | 6/2004 |

* cited by examiner

*Primary Examiner*—Michael P. Woodward
*Assistant Examiner*—Eric E. Silverman

(57) ABSTRACT

The present invention is directed to parenterally-administrable microparticles for providing sustained-release of a therapeutic agent in the body, where the microparticles include a polymeric core containing a therapeutically effective amount of a therapeutic agent disposed therein, a first film encapsulating the core, the first film prepared from a first biodegradable polymer soluble in an appropriate solvent therefore, and a second film encapsulating the core and the first film, the second film prepared from a biodegradable polymer soluble in an appropriate solvent therefore, wherein the first film is insoluble in the solvent used to prepare the second film, and to parenterally-administrable compositions containing such microparticles dispersed in a suitable carrier therefore.

16 Claims, 3 Drawing Sheets

COMPOSITIONS FOR PARENTERAL ADMINISTRATION AND SUSTAINED-RELEASE OF THERAPEUTIC AGENTS

FIELD OF THE INVENTION

The present invention relates to compositions comprising microparticles for parenteral administration and sustained-release in the body of therapeutic agents such as proteins, peptides and drugs.

BACKGROUND OF THE INVENTION

Many drugs, proteins and peptides for use in medical therapy are susceptible to degradation at the site of administration. In addition, many of these therapeutic agents have very short in vivo half-lives. Consequently, multiple injections or multiple oral doses are required to achieve desirable therapy. It is desirable to increase the therapeutic efficacy of these therapeutic agents containing active ingredients by using parenterally administrable formulations that provide controlled release of the therapeutic agents.

A formulation intended for parenteral use must meet a number of requirements in order to be approved by the regulatory authorities for use in humans. It must be biocompatible and/or biodegradable and/or bioabsorbable and all substances used and their degradation products should be non-toxic. By biodegradable, it is meant that the materials are degraded or broken down under physiological conditions in the body such that the degradation products are excretable or absorbable by the body. In addition, particulate therapeutic agents intended for injection must be small enough to pass through the injection needle, which means that they preferably should be smaller than 200 microns. The agent should not be degraded to any large extent in the formulation during production or storage thereof, or after administration, and should be released in a biologically active form with reproducible kinetics.

Various dosage forms have been proposed for therapeutic agents that require parenteral administration. For example, an agent may be microencapsulated by a phase separation process using a coacervation agent such as mineral oil, vegetable oils or the like, resulting in the formation of a microparticle containing the agent.

Another microencapsulation method entails formation of a three-phase emulsion containing a therapeutic agent, a polymer and water. A drying step yields microparticles of the agent microencapsulated in the polymer.

Also reported is the formation of microparticles by spray drying, rotary disc or fluidized bed techniques combining biodegradable polymers and therapeutic agents.

As mentioned above, there is a need to control the release of the microencapsulated therapeutic agent from a parenterally administrable sustained release formulation of microparticles. Often, the initial release rate of agent is high. This is known as the initial burst of the agent from the microparticle. In many of the controlled release systems based on biodegradable polymers, the release rate and initial burst of the therapeutic agent is largely dependent on the amount of agent incorporated into the microparticle. This is due to the formation of channels in the microparticles at higher agent loadings.

A well-known way of controlling the release of a therapeutic agent from a solid core is to apply a synthetic, biodegradable polymer coating that produces a rate-controlling film on the surface of the core particles. The release rate and initial burst of the therapeutic agent is controlled by factors including the thickness of the coating, the diffusivity of agent through the synthetic polymer comprising the coating, and the rate of biodegradation of the polymer.

Often, the method of applying the coating to the therapeutic agent particle requires use of organic solvents to dissolve the polymer used in the coating prior to the coating process. This is done in cases where the melting temperature of the polymer is high enough to detrimentally affect in the performance of the agent. The coating process typically involves dissolving the synthetic, biodegradable polymer in an organic solvent to form a solution, spray coating or fluidized-bed coating the solutions onto the microparticles, and evaporating the solvent.

Synthetic polymers utilized in coatings may include aliphatic polyesters, alkyd-type polyesters, polyanhydrides and poly(orthoester)s. Synthetic absorbable polymers typically degrade by a hydrolytic mechanism. Such synthetic absorbable polymers may include homopolymers, such as poly(glycolide), poly(lactide), poly(epsilon-caprolactone), poly(trimethylene carbonate) and poly(para-dioxanone); and copolymers, such as poly(lactide-co-glycolide), poly(epsilon-caprolactone-co-glycolide), and poly(glycolide-co-trimethylene carbonate). The polymers may be statistically random copolymers, segmented copolymers, block copolymers or graft copolymers. Alkyd-type polyesters prepared by the polycondensation of a polyol, polyacid and fatty acid are also useful as coatings on the surface of the core particles.

Proteins, consisting of amino acids, are large molecules that typically are dependant on a well-defined three-dimensional structure for many of their properties, including biological activities and immunogenicity. Their three-dimensional structures can be destroyed relatively easily by exposure to organic solvents, which can affect their biological activity. Thus, a drawback in connection with the use of synthetic, biodegradable polymers for sustained-release of proteins is the requirement to utilize organic solvents to dissolve the biodegradable polymers, with the associated risk of compromising the stability of the protein.

There is a need to develop a microparticle that can reduce exposure of the therapeutic agent to organic solvents that are used to dissolve the coating polymers; can control the release rate of active agent; allow production to be carried out with standard pharmaceutical equipment; and that can be administered parenterally. The present invention satisfies that need.

SUMMARY OF THE INVENTION

The present invention is directed to parenterally-administrable microparticles for providing sustained-release of a therapeutic agent in the body, where the microparticles comprise a core containing a therapeutically effective amount of a therapeutic agent, a first film encapsulating the core, the first film comprising a first biocompatible, biodegradable polymer, and a second film encapsulating the core and the first film, the second film comprising a second biocompatible, biodegradable polymer soluble in an suitable solvent therefore, wherein the first film is insoluble in and impervious to the solvent for the second polymer. The invention also is directed to parenterally-administrable compositions comprising such microparticles and a biocompatible carrier suitable for the microparticle.

DETAILED DESCRIPTION OF THE INVENTION

Figure 1:
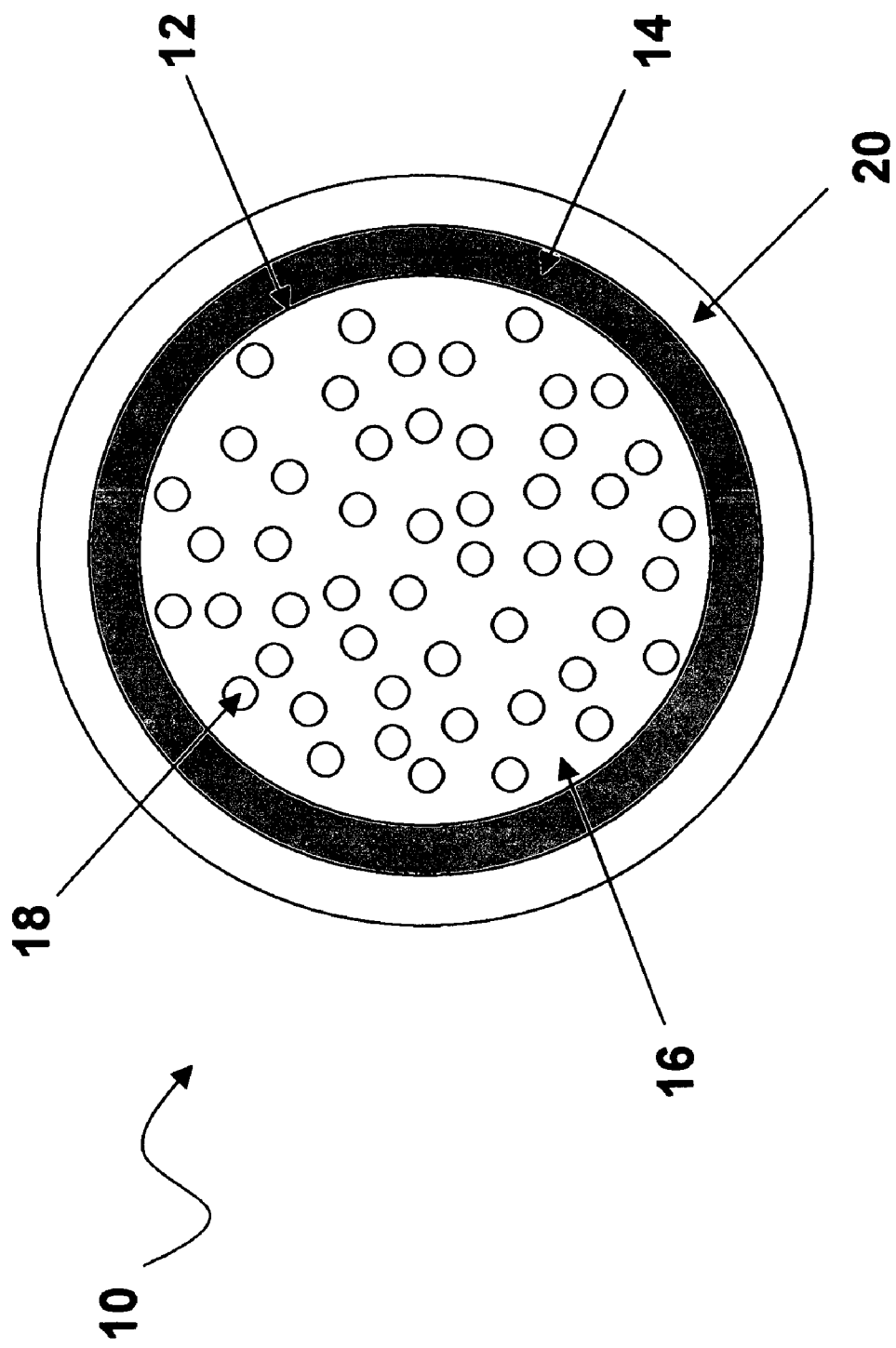
FIG. 1 is schematic cross-section of a microparticle of the present invention.

Microparticles and compositions containing the microparticles are provided where the microparticles comprise a core containing a therapeutically effective amount of a therapeutic agent encapsulated by first and second biocompatible, biodegradable films as described in detail herein. By therapeutically effective amount it is meant that the agent will be present in an amount effective to produce or achieve the pharmaceutical or biological affect intended of the particular therapeutic agent upon release into the body. The presence and selected compositions of the respective films provide for controlled, sustained release of the therapeutic agent in the body, while avoiding premature release or degradation of the therapeutic agent prior to administration in the body.

In certain embodiments of the present invention, the core may consist essentially of the therapeutic agent. In other embodiments of the invention, the core may comprise the therapeutic agent in combination with other ingredients, such as biocompatible, pharmaceutically suitable carriers and/or processing excipients, to aid in formation of the microparticles and/or administration of the microparticles within the body.

In preferred embodiments of the present invention, the microparticle core will contain a biocompatible, biodegradable continuous polymeric phase having a therapeutically effective amount of a therapeutic agent dispersed there through. The polymeric phase serves as a carrier or reservoir for the therapeutic agent. The polymer used as the carrier will be dissolved or degraded by physiologic fluids once administered in the body such that the agent may be release in a controlled manner upon contact of the core to physiologic fluids.

The therapeutic agent may be insoluble in the polymer used to prepare the carrier phase of the core. In such embodiments, the polymer may be melted and the particles of the therapeutic agent dispersed through the molten polymer by means for making particles as disclosed herein, so as to provide a substantially homogeneous dispersion of the solid agent particles through the polymer. Upon cooling, a solid, continuous polymeric phase comprising the agent dispersed there through is provided.

In other embodiments, the therapeutic agent may be soluble in the polymer used to make the carrier phase. In such embodiments, providing that dissolving the therapeutic agent does not detrimentally affect its therapeutic efficacy, the polymer may be melted and the agent dissolved in the molten polymer and mixed so as to provide a homogenous distribution of the agent through the polymer melt. Upon cooling, the core is provided having the agent homogenously mixed through the polymer carrier phase.

A first film comprising a first biocompatible, biodegradable polymer encapsulates the microparticle core. By biodegradable, it is meant that the film or polymer is degraded by physiologic fluids in the body such that the degradation products either are resorbable by or excretable from the body. The first biodegradable polymer is soluble in inorganic solvents, such as water and alcohol. As described herein, the first film is insoluble and impervious to the organic solvent used to prepare and apply the second polymer. This prevents the therapeutic agent in the microparticle core from being contacted by the solvent used in applying the second film, thus avoiding any affect on the core and agent by the solvent. The first film will be dissolved or degraded by physiologic fluids once contacted by body fluids, thus exposing the microparticle core to the physiologic fluids. This in turn permits the therapeutic agent to be released into the body or, where the polymer carrier phase is present, permits contact of the polymer phase with physiologic fluids, where it is dissolved or degraded, thereby providing controlled release of the therapeutic agent from the microparticle core.

A second film comprising a second biodegradable polymer, different from the first biodegradable polymer, encapsulates both the core having the therapeutic agent contained therein and the first film. The second biodegradable polymer is soluble in organic solvents. The second film serves to control the release rate of the therapeutic agent from the polymeric core via its own rate of biodegradability in the body. The particular biodegradability rate required for the particular circumstance may be controlled by selection of the appropriate biodegradable polymer for the second film and the amount of film applied to the microparticle core, i.e. thickness of the film applied. As the second film is degraded, physiological fluids contact and degrade the first film, thus exposing the microparticle core to physiological fluids. Upon contact with physiological fluids, the polymeric phase is degraded and the therapeutic agent is released into the body. Again, the particular rate of degradation of the polymer core, and thus the rate of the release of agent, may be controlled by the selection of the appropriate polymer for the particular circumstance. Thus, controlled, sustained release of the therapeutic agent is achieved. As noted above, the organic solvent used to prepare and apply the second polymeric film may detrimentally affect the therapeutic efficacy of the agent. As the first polymer film is insoluble in and impervious to the organic solvent used in preparation and application of the second biodegradable polymer film, its presence prevents the solvent from contacting the microparticle core and adversely affecting the therapeutic agent in the core.

Solvents used to prepare and apply the second film typically may be a common organic solvent such as a halogenated aliphatic hydrocarbon, e.g. methylene chloride, chloroform, and the like. Other solvents include some ketones, e.g. methyl ethyl ketones and acetone, alcohols, aromatic hydrocarbons, e.g. toluene, halogenated aromatic hydrocarbons, ethers, e.g. methyl t-butyl, cyclic ethers, e.g. tetrahydrofuran, ethyl acetate, diethylcarbonate and cyclohexane. The solvents chosen must be capable of dissolving the second biodegradable polymer and, preferably but not necessarily, will be inert with respect to the therapeutic agent dispersed through the core.

Figure 2:
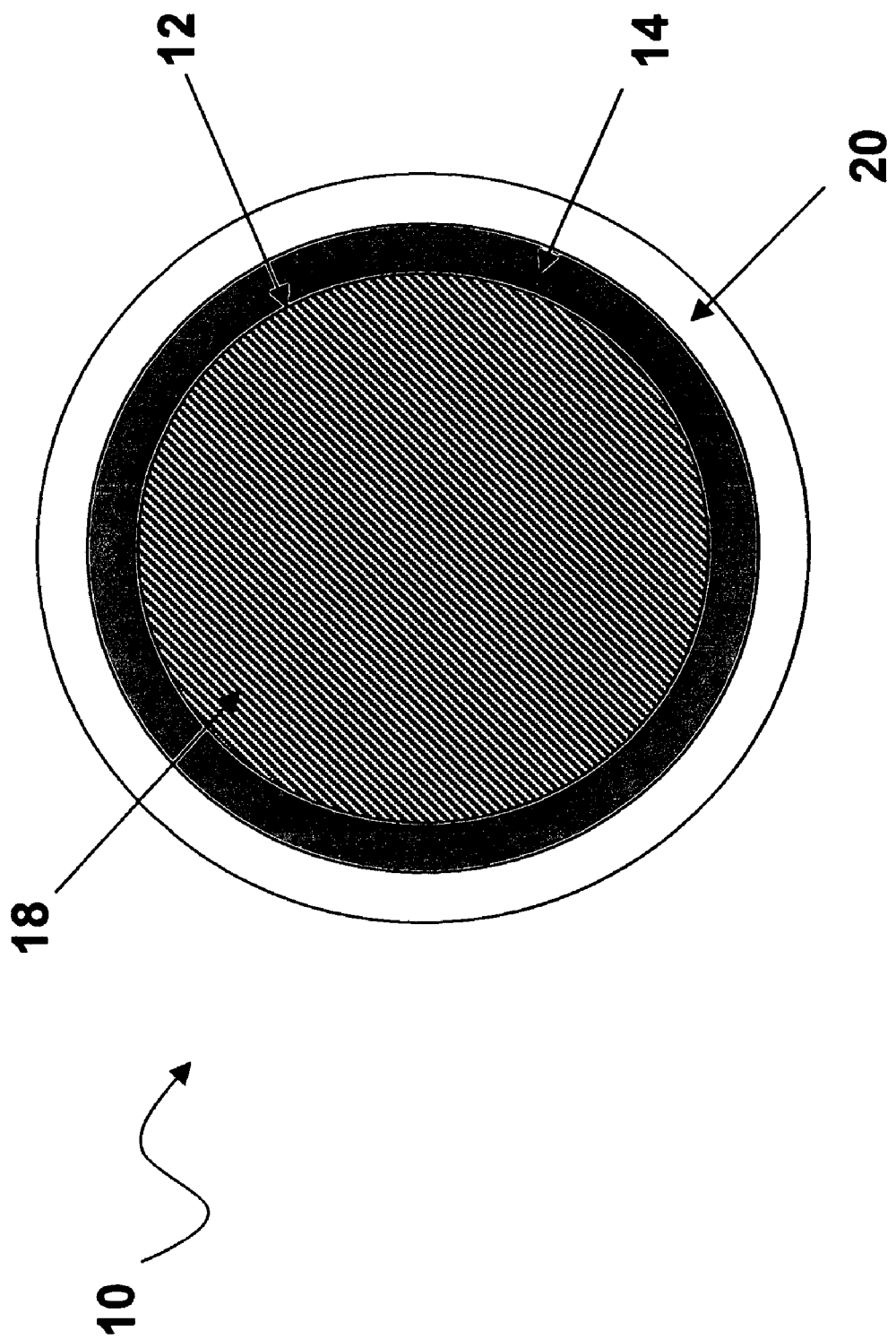
FIG. 2 is schematic cross-section of a microparticle of the present invention.

A schematic cross-section of microparticles of the present invention are shown on FIGS. 1 and 2. FIG. 1 shows microparticle 10 containing core 12, a first film 14 comprised of a first biodegradable polymer, and a second film 20 comprised of a second biodegradable polymer. In a preferred embodiment, core 12 has therapeutic agent 18 substantially homogenously dispersed throughout polymeric carrier 16, comprised of a third biodegradable polymer. FIG. 2 shows another embodiment where core 12 comprises therapeutic agent 12 but does not contain polymeric phase 16. The diameter of microparticle 10 is small enough to pass through an injection needle typically used to administer therapeutic agents to the body, preferably less than about 200 microns. While therapeutic agent 18 is shown as spherical particles suspended in polymeric carrier phase 16, one skilled in the art could envision therapeutic agent 18 as being non-spherical in shape.

Natural or synthetic polymers may be used as the biodegradable polymers in the polymeric carrier phase and the second film, respectively. The polymers used to prepare the polymeric carrier phase and the second film may be the same or different. These polymers may include aliphatic polyesters, polyanhydrides and poly(orthoester)s. Such synthetic polymers include homopolymers, such as poly(glycolide), poly(lactide), poly(epsilon-caprolactone), poly(trimethylene carbonate) and poly(para-dioxanone); and copolymers, such as poly(lactide-co-glycolide), poly(epsilon-caprolactone-co-glycolide), and poly(glycolide-co-trimethylene carbonate). The polymers may be statistically random copolymers, segmented copolymers, block copolymers or graft copolymers. Natural polymers for use as biodegradable polymers in carrier phase 16 and second film 20 include albumin, casein, and waxes such as fatty acid esters of glycerol, glycerol monosterate and glycerol disterate.

Preferably, the synthetic, biocompatible polymers used as the polymers in the carrier and second film are alkyd polymers. The alkyd polymers are in the form of a polymeric wax. The polymeric waxes utilized in the present invention are the reaction product of a polybasic acid or derivative thereof, a fatty acid, and a polyol, and may be classified as alkyd polyester waxes. As used herein, a wax is a solid, low-melting substance that is plastic when warm and, due to its relatively low molecular weight, is fluid when melted. Preferably, the polymeric waxes of the present invention are prepared by the polycondensation of a polybasic acid or derivative thereof and a monoglyceride, wherein the monoglyceride comprises reactive hydroxy groups and fatty acid groups. The expected hydrolysis byproducts are glycerol, dicarboxylic acid(s), and fatty acid(s), all of which are biocompatible. The polymeric waxes comprise an aliphatic polyester backbone with pendant fatty acid ester groups that crystallize rapidly, depending on the fatty acid chain length, and exhibit relatively low melting points, e.g. less than about 100° C., preferably less than about 70° C. More preferably, the melting point of the polymeric wax will be between about 25° C. and about 70° C. Typically, the polymeric wax used in the present invention will be a solid at room temperature.

Fatty acids used to prepare polymeric waxes utilized in the present invention may be saturated or unsaturated and may vary in length from $C_{10}$ to $C_{30}$. Examples of such fatty acids include, without limitation, stearic acid, palmitic acid, myrisitic acid, caproic acid, decanoic acid, lauric acid, linoleic acid and oleic acid.

Polyols that can be used to prepare the polymeric waxes include, without limitation, glycols, polyglycerols, polyglycerol esters, glycerol, sugars and sugar alcohols. Glycerol is a preferred polyhydric alcohol due to its abundance and cost.

Monoglycerides which may be used to prepare polymeric waxes utilized in the present invention include, without limitation, monostearoyl glycerol, monopalmitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides include monostearoyl glycerol, monopalmitoyl glycerol and monomyrisitoyl glycerol.

Polybasic acids that can be used include natural multifunctional carboxylic acids, such as succinic, glutaric, adipic, pimelic, suberic, and sebacic acids; hydroxy acids, such as diglycolic, malic, tartaric and citric acids; and unsaturated acids, such as fumaric and maleic acids. Polybasic acid derivatives include anhydrides, such as succinic anhydride, diglycolic anhydride, glutaric anhydride and maleic anhydride, mixed anhydrides, esters, activated esters and acid halides. The multifunctional carboxylic acids listed above are preferred.

Natural or synthetic polymers may be used as the first biodegradable polymer in the first film. These polymers may include polymers selected from the group consisting of starch and crosslinked starch; simple sugars such as glucose, ficoll, and polysucrose; polyvinyl alcohol; gelatine; modified celluloses such as hydroxymethyl cellulose, hydroxyethyl cellulose, hydroxypropyl cellulose, hydroxypropylethyl cellulose, hydroxypropyl-methyl cellulose, sodium carboxymethyl cellulose, and cellulose acetate; sodium alginate; polymaleic anhydride esters; polyortho esters; polyethyleneimine; glycols such as polyethylene glycol, methoxypolyethylene glycol, and ethoxypolyethylene glycol, polyethylene oxide; poly(1,3 bis(p-carboxyphenoxy) propane-co-sebacic anhydride; N,N-diethylaminoacetate; and block copolymers of polyoxyethylene and polyoxypropylene. The preferred polymer for use as the first biodegradable polymer in the first film is hydroxypropyl-methyl cellulose, or HPMC.

In a preferred embodiment of the invention, the third biodegradable polymer used as pharmaceutical carrier phase 16 is poly(monostearoyl glycerol-co-succinate), or poly (MGSA); the first biodegradable polymer is the water-soluble, film-forming polymers hydroxypropyl-methylcellulose (HPMC); and the second biodegradable polymer is poly(MGSA).

To form the core of the microparticle, the polymer used as the pharmaceutical carrier is mixed with a therapeutically effective amount of the therapeutic agent. Common microencapsulation methods include rotating disk, spray drying, fluidized bed, or three-phase emulsion techniques may be used to prepare the microparticles.

The preferred technique for preparing the therapeutic agent-containing core of the present invention is the rotating disk technique. The polymer used as the pharmaceutical carrier in the core is blended with the therapeutic agent at a temperature above the melting point of the polymer. The blend is then fed at a controlled rate to the center of a rotary disk that is heated to ensure that the blend remains in a liquid state on the surface of the disk. The rotation of the disk causes a thin liquid film of agent/polymer blend to be formed on the surface the disk. The liquid film is thrown radially outward from the surface of the disk and droplets solidify before they are collected. The processing is done under a nitrogen blanket to prevent polymer degradation at the elevated temperatures. The core particles made using this process are usually spherical, but may be irregularly shaped. They can vary in size from 0.5 micron to approximately 250 microns in diameter, though typically they have a mean particle size of about 50–150 microns.

To prevent the direct contact of the organic solvent used in to prepare and apply the second film with a therapeutic agent in the core that may be detrimentally affected by the solvent, the first film is applied between the core and the second coating. The first film may be applied using conventional fluidized bed coating processes. In the fluidized bed coating process, microparticles formed as described above are first suspended in an upwardly-moving gas stream in a coating chamber. The polymer used in the first film, dissolved in a solvent, or, preferably as a melt, is sprayed into the moving fluid bed of microparticles to coat the microparticles. The coated microparticles are recovered, and any residual solvent is removed.

The second film of the microparticles, which is used to control the rate of release of the therapeutic agent from the core of the microparticle, is applied by any method that is capable of applying a coating onto microparticles. Preferably, the fluidized bed coating process described above is utilized to apply the second film once the first film is dry.

The molecular weight of the polymers used as the second film should be high enough so that the polymers are effective in forming films. The amount of polymer in the first film is preferably from about 0.1 to 50 percent of the weight of the core, more preferably from about 0.5 to 10 percent. In preferred embodiments, the first biodegradable polymer comprises from about 0.5% to 50%, more preferably about 25 percent by weight of the total weight of the third biodegradable polymer in the core of the microparticle. The amount of polymer in the second film is preferably from about 0.5 to 200 percent of the weight of the core, more preferably from about 5 to 100 percent. The amount of therapeutic agent in the microparticle ranges from about 0.1 to about 50 percent by weight of the microparticle, preferably from about 1 to about 25 percent by weight of the microparticle.

Additives can also be incorporated into the second film. These include film property modifying agents and release controlling agents. Film property modifying agents may include plasticizers, such as triethyl-citrate, triacetin, polyethyleneglycol, and polyethyleneoxide. Release controlling agents may include, for instance, inorganic bases such as sodium hydroxide, potassium hydroxide, sodium carbonate, and potassium carbonate, organic bases such as ethanol amine, diethanole amine, triethanole amine, lidocaine, and tetracaine, inorganic acids such as ammoniumsulfate and ammonium chloride, organic acids such as citric acid, lactic acid, glycolic acid, and ascorbic acid, and solid soluble substances which, upon release, create pores in the coating (such as crystals of sodium chloride, glucose, mannitol, and sucrose).

After the application of the second film, additional materials could also be is applied onto the microparticles in order to further modify the properties thereof or to facilitate the handling thereof. Properties include color, stability of both drug and microparticles, release profiles, separation of incompatible drugs, size, physical strength, and dispersability in liquid carrier. Examples of such materials are mannitol, sucrose and sodium chloride.

The variety of therapeutic agents that can be used in the coated microparticles of the invention is vast. The therapeutic agent may be chosen from a wide variety of chemical compounds, such as lipophilic and/or hydrophilic active agents, including peptides and proteins. Therapeutic agents of particular interest in this invention are proteins, peptides, growth factors, drugs and biologically active substances that are sensitive to, or unstable in, the presence of organic solvents. However, the invention is not limited to the presence of such substances.

In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics.

Rapamycin, risperidone, and erythropoietin are several bioactive agents that may be used in drug delivery matrices of the present invention.

The active proteins or peptides include cytokines, such as interleukins, G-CSF, M-CSF, GM-CSF or LIF. Other active proteins or peptides include interferons, erythropoetins, cyclosporins, and hormones, or their analogues, such as octreotide.

The following examples further describe the materials and methods used in carrying out the invention. The examples are not intended to limit the invention in any manner. Numerous additional embodiments within the scope and spirit of the invention will become readily apparent to those skilled in the art.

In the examples below, the synthesized polymers were characterized via differential scanning calorimetry (DSC), gel permeation chromatography (GPC), and nuclear magnetic resonance (NMR) spectroscopy. DSC measurements were performed on a 2920 Modulated Differential Scanning Calorimeter from TA Instruments using aluminum sample pans and sample weights of 5–10 mg. Samples were heated from room temperature to 100° C. at 10° C./minute; quenched to −40° C. at 30° C./minute, followed by heating to 100° C. at 10° C./minute. For GPC, a Waters System with Millennium 32 Software and a 410 Refractive Index Detector were used. Molecular weights were determined relative to polystyrene standards using THF as the solvent. Proton NMR was obtained in deuterated chloroform on a 400 MHz NMR spectrometer using Varian software. The in vitro drug release was characterized by spectrophotometer at 272 nm. Concentration of the drug was determined relative to drug standards using water as the solvent.

EXAMPLE 1

Synthesis of poly(monostearoyl glycerol-co-succinate)

The copolymer was made in an 8CV Helicone Mixer Manufactured by Design Integrated Technology, Inc. of Warrenton, Va. 2510 grams of monostearoyl glycerol were weighed into a polyethylene bag. 700 grams of Succinic Anhydride were added to a 3-liter glass beaker. Then, 1.4 milliliter of a 0.33 Molar Stannous Octoate solution was drawn into a 2-milliliter glass syringe. All 3 materials were covered and transferred to the 8CV reactor. The stirrer was turned on to 8 rpm reverse for 30 minutes, then the reactor was left under full vacuum for at least 5 hours. The vacuum was 0.43 mm Hg. The oil jacket temperature was set at 180° C. Stirring was set at 8 rpm reverse. The time that the oil jacket inlet temperature had reached 180° C. was recorded as time zero for polymerization. Reaction lasted for 46.5 hours at 180° C. The polymer was discharged into clean aluminum pie pan. Once the solution crystallized, it was deglassed and cleaned of any glass fragments. The polymer was an amber colored solid.

DSC measurements determined a melt temperature of 46.8° C., and a specific heat of 63.57 J/gm. GPC measurement determined a number average molecular weight of 2,932, and a weight average molecular weight of 38,422. The $^1$H NMR showed the following peaks: δ 0.86 triplet (3H), 1.26 multiplet (28H), 1.61 multiplet (2H), 2.30 multiplet (2H), 2.65 multiplet (4H), 4.16 multiplet (2H), 4.34 multiplet (2H), and 5.28 multiplet (2H).

EXAMPLE 2

In Vitro Sustained Release of Theophylline from Coated Microparticles

Poly(monostearoyl glycerol-co-succinate), or poly (MGSA), polymer was made as described in Example 1. 20 grams of the polymer were placed in a 50-ml beaker and heated to 110° C. to melt the polymer. 6.68 grams of a drug in the form of a powder, Theophylline, sold by Sigma, (St Louis, Mo.), were dispersed and suspended into the polymer melt using a magnetic stirrer to form a 25 percent by weight drug in polymer blend. A gradient heating mechanism was used to limit the exposure of the drug to the polymer melt at elevated temperature to a few seconds.

The drug/polymer blend was then converted to microparticle cores on a rotating disk apparatus. The drug/polymer blend was first equilibrated at 110° C. and then fed at a controlled rate of 3.5 grams/sec to the center of a 4-inch rotary disk that was run at 8000 RPM. The disk surface was heated using an induction heating mechanism to 130° C. to ensure that the drug/polymer blend was in a liquid state on the surface of the disk. The rotation of the disk caused a thin liquid film of drug/polymer blend to be formed on the surface of the disk. The liquid film was thrown radially outward from the surface of the disk and droplets solidified upon contact with nitrogen in the rotating disk apparatus chamber to form drug/polymer core microparticles. The processing was done under a nitrogen blanket to prevent polymer degradation at elevated temperatures. The solid core micropareticls were then collected using a cyclone separator. The core microparticles made using this process had a mean particle size of about 100 microns.

The microparticle cores were then coated with hydroxypropyl methylcellulose (HPMC) in batches using a fluidized bed coater (Niro MP-Micro precision coater, Aeromatic-Fielder Ltd., Eastleigh Hampshire, UK). A sugar/microparticle batch was first prepared by blending 45 grams of sugar spheres (Paulaur Co., Cranbury, N.J.) with a size range of between 40 and 60 mesh, and 5 grams of the theophylline loaded poly(MGSA) core microparticles. The sugar spheres and microparticle cored were blended in a Wurster Chamber (Niro MP-Micro precision coater, Aeromatic-Fielder Ltd., Eastleigh Hampshire, UK). This method was used to create four 50-gram sugar/microparticle batches. For each batch, a coating solution of HPMC was then prepared by dissolving 2.5 grams of HPMC, sold under the tradename OPADARY, by Colorcon, (West Point, Pa.), powder in 50 milliliters of water. The coating solution was gently agitated during the coating process. 52.5 grams of HPMC/water coating solution was added to the fluidized coater. The coating parameters were set as follows:

| Atomization pressure | 3.0 Bar |
|---|---|
| Atomization nozzle | 0.8 mm |
| Inlet temperature | 60.0° C. |
| Outlet temperature | 31–32° C. |
| Flow rate of coating solution | 2.0 gram/min |
| Fluidization air volume | 2.50–3.50 m$^3$/hr |

Particles were dried in the Wurster Chamber by blowing air for 20 minutes. The HPMC coating on the microparticle cores was approximately 5 weight percent of the weight of the core.

After the HPMC coating was completely dried, a second coating was applied to three of the four sugar/microparticle batches. The second coat, a poly(MGSA) polymer, was applied using the above fluidized bed coater. First, a coating solution was prepared by dissolving 25.0 grams of poly (MGSA) polymer in 100.0 grams of chloroform. 50 grams of HPMC-coated sugar/microparticles from the one batch were loaded into the fluidized bed coater with 25 grams of poly(MGSA)/chloroform coating solution. The coating parameters were set as follows:

| Atomization pressure | 2.0 Bar |
|---|---|
| Atomization nozzle | 0.8 mm |
| Inlet temperature | 55.0° C. |
| Outlet temperature | 31–32° C. |
| Flow rate of coating solution | 0.5 gram/min |
| Fluidization air volume | 2.50–3.50 m$^3$/h |

After drying the poly(MGSA) coated microparticles were collected and sieved to 40 to 60 mesh and stored in a vacuum oven. The poly(MGSA) coated microparticles thus prepared contained about 10 weight percent coating of poly(MGSA).

Two more batches of poly(MGSA) coated microparticles were also prepared as with minor changes to the procedure described above. The second batch used 50 grams of HPMC-coated sugar/microparticles and 50 grams of poly (MGSA)/chloroform coating solution in the fluidized bed coater, and resulted in poly(MGSA) coated microparticles with a 20 weight percent coating of poly(MGSA). The third batch used 50 grams of HPMC-coated sugar/microparticles and 75 grams of poly(MGSA)/chloroform coating solution in the fluidized bed coater, and resulted in poly(MGSA) coated microparticles with a 30 weight percent coating of poly(MGSA).

In vitro release studies were performed with the 10, 20, and 30 percent poly(MGSA) coated microparticles in a buffer medium under physiological conditions, as well as with the beads with no poly(MGSA) coating. For each in vitro release study, approximately 20 milligrams of microparticles were placed in 50 milliliter test tubes. 30 milliliters of phosphate buffered saline solution was added to the test tubes. The test tubes were placed in a constant temperature water bath, and kept at 37° C. for the duration of the test. To determine drug release from the microparticles at each time point, 5 milliliters of buffer was removed and filtered through a 0.2 micron filter. The amount of drug released was determined by spectrophotometer measurements at 272 nm on an HP8453 instrument against Theophylline standards.

Figure 3:
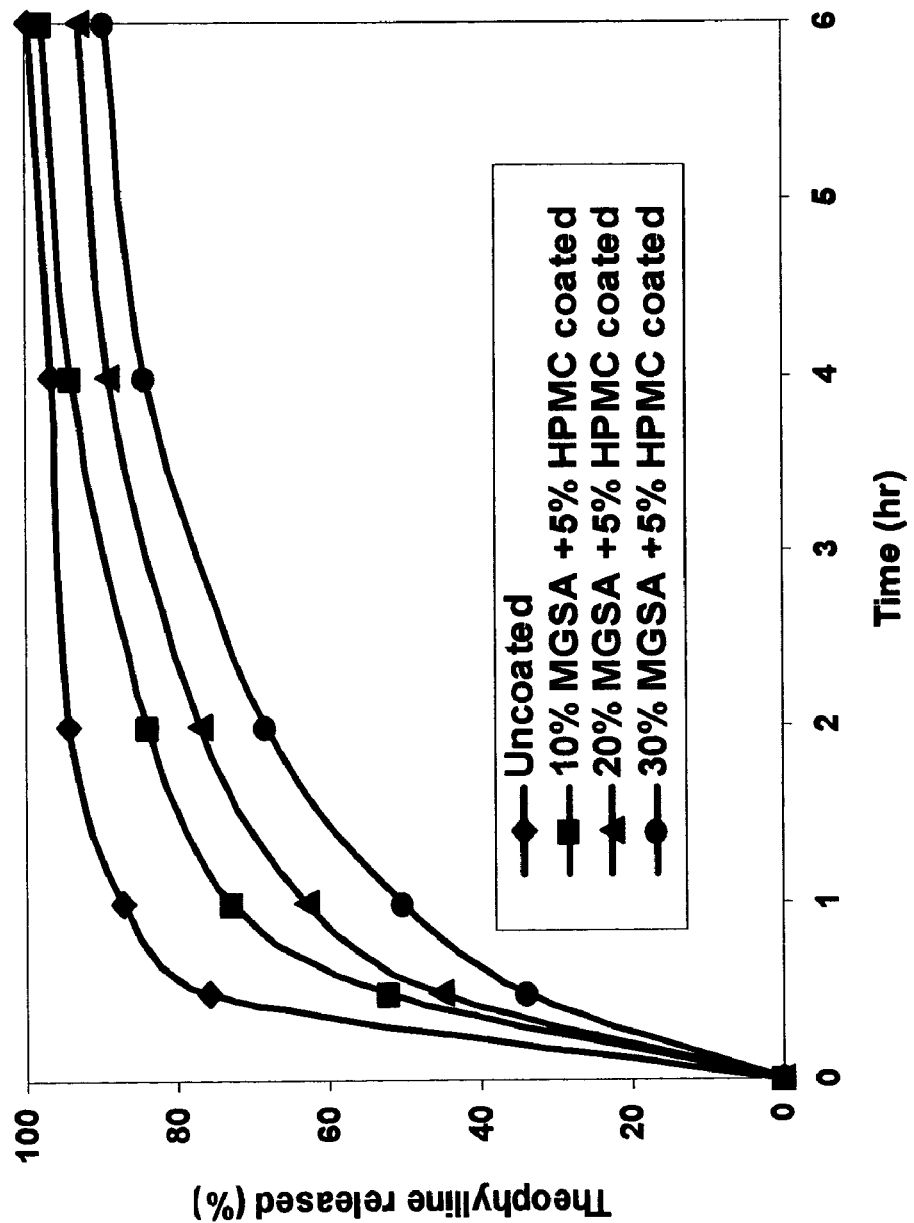
FIG. 3 is a plot of sustained-release of theophylline from microparticles of the present invention.

In vitro release of theophylline from the various microparticles is shown on FIG. 3. The figure shows that by increasing the poly(MGSA) second coating level from 0 to 30 weight percent, the theophylline release from coated microparticles was significantly reduced. A burst can be seen at all poly(MGSA) coating levels, but decreased as the level of poly(MGSA) increased.

We claim:

1. A parenterally-administrable microparticle for providing sustained-release of a therapeutic agent in the body, comprising:
   a core comprising a therapeutically effective amount of a therapeutic agent,
   a first film comprising a first biodegradable polymer comprising hydroxypropyl-methyl cellulose encapsulating said core, and
   a second film applied to said first film and encapsulating said first film and said core, said second film comprising a second biodegradable polymer comprising an alkyd polyester wax soluble in an appropriate solvent for said second polymer, wherein said core comprises a third biodegradable polymer comprising an alkyd polyester wax having said therapeutic agent dispersed there through, and said first film is insoluble in and impervious to said solvent for said second biodegradable polymer.

2. The microparticle of claim 1 wherein said third biodegradable polymer and said second biodegradable polymer are the same.

3. The microparticle of claim 1 wherein said third biodegradable polymer and said second polymer are different.

4. The microparticle of claim 2 wherein said second and third biodegradable polymers comprise poly(monostearoyl glycerol-co-succinate) and said first biodegradable polymer comprises hydroxypropyl-methyl cellulose.

5. The microparticle of claim 1 comprises from about 0.1 to about 50 percent by weight of said therapeutic agent.

6. The microparticle of claim 5 wherein said therapeutic agent is selected from the group consisting of proteins, peptides, growth factors, and drugs.

7. The microparticle of claim 1 comprising from about 0.1 to about 50% of said first film by weight of said core.

8. The microparticle of claim 1 comprising from about 0.5 to about 200% of said second film by weight of said core.

9. Compositions for patenteral administration and sustained-release of therapeutic agents' comprising:
   a microparticle, said microparticle comprising,
      a core comprising a therapeutically effective amount of a therapeutic agent,
      a first film comprising a first biodegradable polymer comprising hydroxypropyl-methyl cellulose encapsulating said core, and
      a second film applied to said first film and encapsulating said first film and said core, said second film comprising a second biodegradable polymer comprising an alkyd polyester wax soluble in an appropriate solvent for said second polymer, wherein said core comprises a third biodegradable polymer comprising an alkyd polyester wax having said therapeutic agent dispersed there through and said first film is insoluble in and impervious to said solvent for said second biodegradable polymer, and;
   a biocompatible suitable carrier for said microparticle.

10. The composition of claim 9 wherein said third biodegradable polymer and said second biodegradable polymer are the same.

11. The composition of claim 9 wherein said third biodegradable polymer and said second polymer are different.

12. The composition of claim 10 wherein said second and third biodegradable polymers comprise poly(monostearoyl glycerol-co-succinate) and said first biodegradable polymer comprises hydroxypropyl-methyl cellulose.

13. The composition of claim 9 comprising from about 0.1 to about 50 percent by weight of said therapeutic agent.

14. The composition of claim 13 wherein said therapeutic agent is selected from the group consisting of proteins, peptides, growth factors, and drugs.

15. The microparticle of claim 9 comprising from about 0.1 to about 50% of said first film by weight of said core.

16. The microparticle of claim 9 comprising from about 0.5 to about 200% of said second film by weight of said core.

* * * * *